(12) United States Patent
Kuth et al.

(10) Patent No.: US 8,190,445 B2
(45) Date of Patent: May 29, 2012

(54) SYSTEM TO DETECT, ADMINISTER AND/OR EVALUATE CONFIGURATION DATA DESCRIBING THE HARDWARE AND/OR SOFTWARE CONFIGURATION OF DIFFERENT DEVICES

(75) Inventors: Rainer Kuth, Hoechstadt (DE);
Sebastian Schmidt, Weisendorf (DE);
Sabine Schaeffer-Kundler, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 293 days.

(21) Appl. No.: 12/561,555

(22) Filed: Sep. 17, 2009

(65) Prior Publication Data
US 2010/0094700 A1    Apr. 15, 2010

(30) Foreign Application Priority Data

Sep. 17, 2008  (DE) .......................... 10 2008 047 576

(51) Int. Cl.
*G06Q 10/00*    (2012.01)
(52) U.S. Cl. ........................................ 705/1.1
(58) Field of Classification Search .................. None
See application file for complete search history.

(56) References Cited

U.S. PATENT DOCUMENTS

| | | | |
|---|---|---|---|
| 6,363,282 | B1 | 3/2002 | Nichols et al. |
| 2005/0135306 | A1* | 6/2005 | McAllen et al. ............. 370/329 |
| 2006/0026205 | A1* | 2/2006 | Butterfield ................. 707/104.1 |
| 2006/0106649 | A1* | 5/2006 | Eggers et al. ..................... 705/3 |
| 2008/0004991 | A1 | 1/2008 | Aikens et al. |
| 2009/0171175 | A1* | 7/2009 | Li et al. ......................... 600/324 |
| 2011/0066260 | A1* | 3/2011 | Condurso et al. .............. 700/83 |

FOREIGN PATENT DOCUMENTS

DE    10 2005 013 041 A1    6/2006

\* cited by examiner

*Primary Examiner* — Jonathan Ouellette
(74) *Attorney, Agent, or Firm* — Schiff Hardin LLP

(57) ABSTRACT

A system for detection, administration and/or evaluation of configuration data describing the hardware or software configuration of different (in particular medical technology) devices has a central database (in particular manufacturer-spanning central database) the configuration data stored therein, which is connected to a network (in particular the Internet via at least one software unit (fashioned as a programming interface and/or Internet platform), which enables a role-specific access to the database via role-based interfaces. An operator role and/or an end user role (in particular a referrer and/or patient role) and/or a manufacturer role are provided as roles.

17 Claims, 1 Drawing Sheet

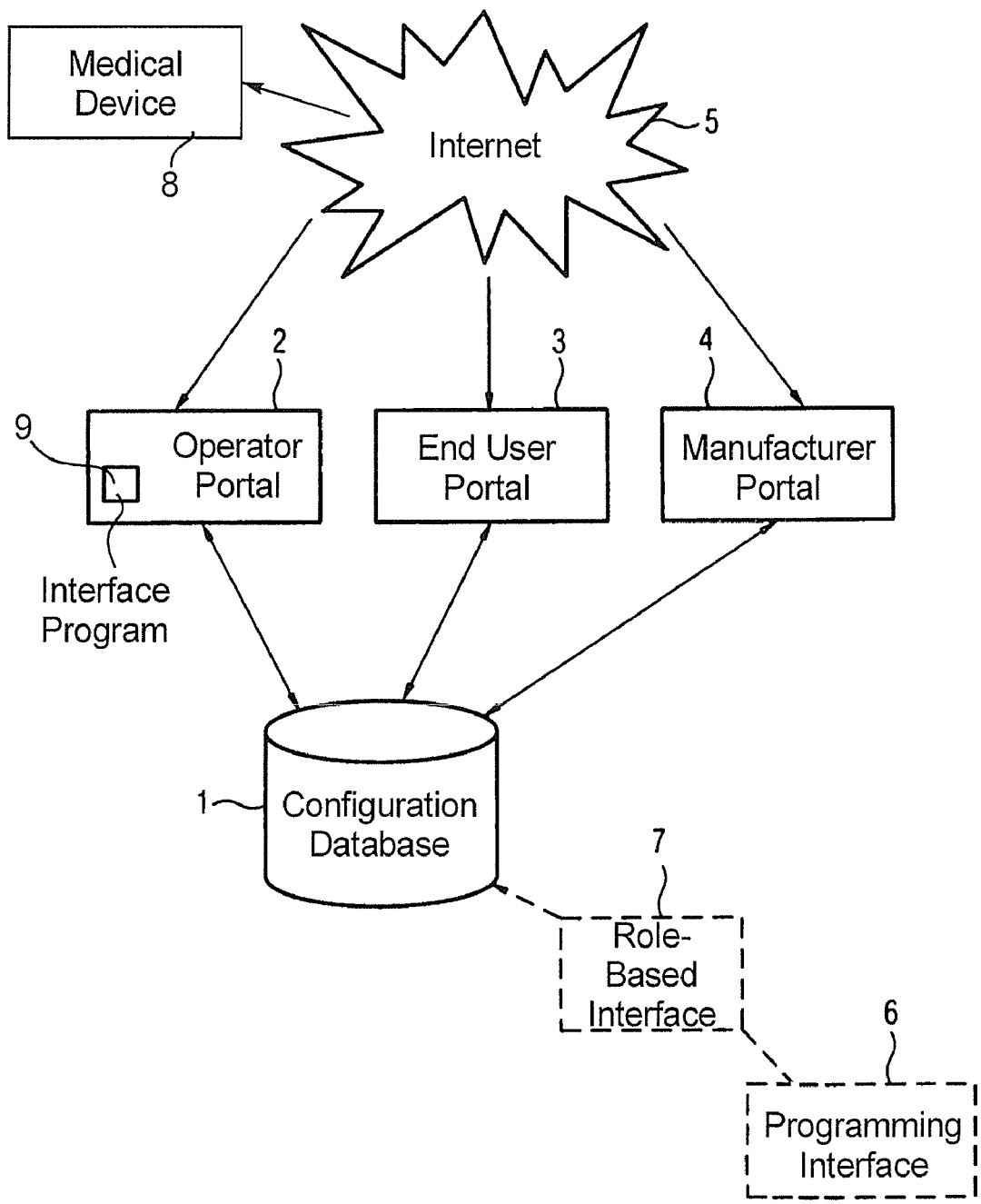

SYSTEM TO DETECT, ADMINISTER AND/OR EVALUATE CONFIGURATION DATA DESCRIBING THE HARDWARE AND/OR SOFTWARE CONFIGURATION OF DIFFERENT DEVICES

BACKGROUND OF THE INVENTION

1. Field of the Invention

The present invention concerns a system to detect, administer and/or evaluate configuration data describing the hardware and/or software configuration of different (in particular medical technology) devices.

2. Description of the Prior Art

For a variety of technical devices, in particular for medical technology devices, several systems are known to assist in maintenance and support as well as for information exchange among customers. For example, it is known that software or firmware updates can be downloaded (for example from an Internet platform of the manufacturer) and installed on such devices. Customer-to-customer systems (often abbreviated as "c2c") allow the exchange of information between operators of devices is well known. For example, Internet platforms are known in which operators of magnetic resonance systems can exchange configurations, examination protocols or sequences among one another.

Particularly in the medical technology field, a large number of possibilities for personal adjustment and/or modification of the complex devices exist with regard to both software and hardware. Operators modify the purchased apparatuses via upgrades and expansions and resell apparatuses or parts thereof, such that the internal databases of the manufacturers become less accurate with the passage of time as to the actual state of the device. This makes it difficult for the manufacturer to accurately provide the customers with information and upgrades for their systems.

For the operators of the devices, it becomes ever more difficult to exchange information, tools or the like since the different equipment states of the apparatuses (thus their different configurations) must be taken into account for that purpose. For example, if Hospital A would like to pass an internally-developed examination protocol to Hospital B, it is often not clear whether the technical equipment at Hospital B is sufficient to implement this protocol at all.

This problem cannot be remedied through the manufacturers' own databases of the sold devices, since, as noted above, ever greater deviations of the installed base (the entirety of the installed and operated devices) from these databases occurs with time due to resales, modifications and the like. For example, expansions or replacement parts from third party manufacturers can be purchased, and software updates that have been sent to the customer may not have been actually input.

For the end users of the apparatuses (the patients and the referrers, for the most part physicians, in the example of medical technology) it also becomes ever more difficult to identify suitable devices for planned examinations. For example, only a relatively small subset of the magnetic resonance tomography systems available worldwide are suitable for examinations of the heart. However, for a physician or patient there exists no possibility to discover where the nearest suitable system is available.

This lack of transparency increasingly becomes a problem since, due to technical progress, ever more apparatuses will be installed, and ever more equipment variants will be provided for every apparatus. Given a modern medical technology device, for example, there are often significantly more equipment variants available than there are apparatuses of a model series that are manufactured at all, such that it is possible that no single device is the same as any other.

Particularly with regard to combinations of components of various manufacturers, the problem is exacerbated since most known databases or the addressed online communities are manufacturer-specific; this means that they pertain only to the customers and devices or components of the respective manufacturer.

SUMMARY OF THE INVENTION

An object of the present invention is to provide an improved system that enables the urgently needed transparency with regard to the configuration data together with sufficient data protection.

To solve this problem, according to the invention a system is provided for detection, administration and/or evaluation of configuration data describing the hardware or software configuration of different (in particular medical technology) devices, this system having a central data base (in particular a multi-manufacturer central database) containing the configuration data that is connected to a network (in particular the Internet) via at least one software unit (fashioned as a programming interface and/or Internet platform) which enables a role-specific access to the database via role-based interfaces. An operator role and/or an end-user role (in particular a referrer and/or patient role) and/or a manufacturer role are provided as roles for the role-based interface.

According to the invention, a central database is used to store the configuration data of the most varied devices and to keep the configuration data for those devices as current as possible. Although the system is applicable in principle for every type of device, the following specification deals primarily with medical technology devices.

The central database can span across manufacturers—thus contain the configuration data of at least one entire class of devices (for example all magnetic resonance apparatuses) independent of the respective manufacturer—so that even the apparatuses combined from components of multiple manufacturers can be administered. It is then particularly advantageous for the central database to be operated by an independent organization which can prevent misuse by means of data protection functions of the system according to the invention that are described below.

At least one software unit is provided for communication of the central database (which is in particular stored on a computer) with the users, such user ideally being all operators and manufacturers and possibly also end users. This software unit can be a unit or module known as a programmer interface, frequently also called an API (Application Programming Interface). External applications, for example Internet platforms or communities operated by other organizations, can be connected to the database via this programming interface. Alternatively or additionally, an Internet platform that allows a direct access to the database can be provided on the computer itself. Combined embodiments are also conceivable in which an Internet platform is assigned some roles and a programming interface is assigned to others. Naturally, it is also possible to associate both a programming interface and an Internet platform with a role. Arbitrary embodiments are conceivable here, and it should be emphasized again that an Internet platform to access the central database can be enabled both by the operator of the database himself and by additional operators via external access via a programming interface.

As mentioned, the system according to the invention provides a role-specific access to the database, which means that role-based interfaces to the database are provided. More specifically, this means that different user groups (in particular manufacturers, operators and/or end users) respectively have access to a different extent to the central database. In a specific example, this means that operators have the possibility to enter configuration data of their device or devices into the database as precise additional information about these, and at the same time have access to freely provided information (for example tips or use protocols) for devices of other operators. Primarily a querying of the database with regard to the search for a device suitable for an end user's purposes is accorded to the end user role. Manufacturers in their role can access specific (if necessary anonymized) data in the database in order to be able to evaluate these in order to be able to provide suitable support to an operator. In other words, the database is accessible by searchers with respectively different roles according to search rules that are respectively different of the different roles ("searching" herein encompassing data entry).

In a particularly advantageous embodiment, the system according to the invention thus provides three access types clearly separate from one another (namely for manufacturer, operator and user) that respectively receive (via different Internet platforms) an access to the central database that is tailored to their requirements.

If a manufacturer-spanning database is provided, the access of the respective manufacturers to devices and the associated data produced by them can thus additionally be limited in order to prevent corporate espionage. Nevertheless, specific general information (for example the number of devices of a specific class that is in operation or the like) can generally be available.

According to the invention, a common central database is used (in particular on the Internet) with configuration data regarding, in particular, medical technology devices as a common database for (in particular three) online portals that are directed toward manufacturers, end users and operators of the apparatuses. This is achieved by the role-based interfaces that enable a role-based access to the database. All (in particular three) groups or roles thus can benefit from a maximum usage of the database and nevertheless can use online portals (Internet platforms) operating independently and in parallel. The many advantageous usage possibilities of the system according to the invention, in particular with regard to the information of the end users, the data evaluation on the part of the manufacturers, and the data exchange among operators, are explained in detail in the following embodiments of the present invention.

As mentioned, additional useful information can also be stored in the database in addition to the configuration data. Thus additional device information and/or data associated with the configuration data can be stored in the database in addition to the configuration data, in particular the site of the device; and/or information regarding the institution operating the device; and/or the type of use of the device; and/or information regarding the salability of the device; and/or control data, in particular usage protocols of the device; and/or information about the operator. The manner of using this additional information is presented in detail using the particularly advantageous portals utilized as a whole, namely the operator portal, the end user portal and the manufacturer portal, wherein each of these portals can be provided as a software unit (i.e., as an Internet platform) or can be connected via a programming interface.

For example, an operator portal can be provided as a software unit or can be connected via a programming interface, wherein configuration data about devices used at the respective operator and/or additional device information and/or additional device data and/or device-related software unit can be uploaded or downloaded and/or stored in the database in addition to a specific registration via the operator portal. The primary purpose of the operator portal—in addition to the possibility for data exchange between different operators—is accordingly to add data into the database, in particular current configuration data, and/or to add data that should be shared with other operators to the database or to retrieve (in a limited manner) data from the database.

Three advantageous embodiments of the system are presently described for uploading and/or system-side determination of the configuration data. A configuration file generated by an interface program, which is installed or that can be installed on the device, can be uploaded. In another embodiment, the interface program of the respective device can also communicate directly (in particular in a device role) with the database and can keep the configuration data current there. In this preferred embodiment, a special interface program is accordingly used that automatically determines all necessary configuration data and can already provide such data to in the correct format the database indirectly or directly via the operator portal.

Additionally or alternatively, a copy of a screen content of the device (in particular a configuration or status screen) can be uploaded from which the configuration data can be determined via image analysis by the system (for example, a program on the computer also encompassing the database). In practice, every medical technology device has the capability to display a summary of the current hardware and software configuration as a configuration and/or status screen. This can now be saved in a file (for example through the capability provided in most operating systems to store the screen content) and be communicated to the operator portal. The system can determine the configuration data via image analysis (in particular text recognition) via the operator portal—which ultimately is also a software unit, thus a program or even a software package in the sense of the invention—or via a corresponding program associated with the database itself (in particular on the computer containing the database).

In a further embodiment for uploading and/or system-side determination of the configuration data that can likewise be used additionally or alternatively, system data of the device (in particular data determined with the device having a header indicating the configuration of the device and/or log files and/or portions of the system registry) are uploaded, from which the configuration data can be determined by the system. For example, in the field of medical imaging it is typical for image data to be stored according to an industry standard known as the DICOM format, which specifies the configuration of the device used to acquire the image in a header. Most devices additionally generate log files; in addition to this, a great deal about the configuration can be learned from the system registry of an operating system. It is now possible for the system to determine the configuration file on the basis of such files in the sense already presented with regard to the screen content. In this case additional files do not need to be used; rather, files that are present anyway can be utilized.

In an additional advantageous embodiment, purchases and sales of devices can be organizable (tracked) through the operator portal. This not only has the advantage that the operator portal also enables trade with devices between the different operators in addition to the exchange of information, but also allows the "path" a device takes between operators to be directly tracked. In addition, auxiliary devices, accessories, replacement parts and the like are tracked via the operator portal.

An analysis of device configurations and an output of recommendations and/or information can appropriately ensue depending on the analysis result via the operator portal. For example, an operator can upload the relevant configuration data and then select "Analysis". Recommendations can then be provided to the operator, for example with regard to hardware or software configurations that are most advantageous for the operator's purposes, or even software updates and the like. Additional information can also be offered, for example an expanded field of use or auxiliary devices available for purchase. Support is already provided in the operator portal in this manner without direct intervention of the manufacturer, and the operator can additionally make use of additional information of other operators.

In a further embodiment of the system according to the invention, an operator can receive an incentive (in particular in the form of money and/or a software option and/or a tool) as a reward for uploading configuration data. A motivation for the operator to keep his or her configuration data in the database as current as possible is therefore particularly advantageously provided to the operator. As a reward for the uploading of the configuration data the operator can receive a sum of money or bonus points or the like in a manufacturer program. Other conceivable rewards are special software options or also tools that make working with the device simpler for the operator. A number of possibilities are conceivable. In particular, reward can be determined using the quality (in particular the completeness and/or the lack of ambiguity in the ability to be associated with a device class) of the configuration data. The more precise (thus the more qualitatively high-grade) the transmitted configuration data, the more valuable the reward turns out to be.

In addition to the operator portal, an end user portal can also advantageously be provided as a software unit or can be connected via a programming interface, that allows an end user to search for devices according to specific search criteria via a programming interface and/or can in particular receive medical information. As mentioned, in the medical technology field it is primarily physicians or medical facilities (collectively designated as "referrers") and patients that are considered as end users in the sense of the present invention. Both parties search under specific circumstances for medical technology devices suitable for a specific examination (in particular image acquisition devices) that allow the examination to proceed and that should possibly satisfy specific additional criteria. If additional information (for example the location of the device and/or price information for use of the device) is also present in addition to the configuration data determining suitability, a specific search or a suitable device can easily be realized. Specifically with regard to the end user portal, it can be advantageous for an external operated portal that accesses the database in the end user role via a programming interface to encompass with more comprehensive functionality. For example, online portals (Internet platforms) have been proposed that administer medical data of the patients in the manner of an electronic patient file and can also provide medical information, for example the system "Google Health". Via the connection to the system according to the invention, a targeted search for physicians or facilities with specific examination possibilities and devices can be enabled, for example the search for 3 Tesla nuclear magnetic resonance systems with the option for cardiac imaging, the acquisition of the kidneys in close proximity to the location of the patient.

The integration of such a patient portal moreover also has substantial advantages for the operators and the manufacturers. The operators can optimally present the patient with his examination possibilities, and thus can ultimately market via the end user portal. In addition a greater inducement is provided for the operators if the possibility results to also directly inform the end users of the data via a known end user portal. Advantages also result for the manufacturers when the search queries of the end users are also protocolled and, for example, are stored in the database. Demand and market analyses can be created that can guide and optimize the research and development of the manufacturer. For example, it can be established that a specific type of chest examinations is searched for particularly frequently. This market segment thus can be more intensely developed and researched; such information can additionally enter into marketing strategies.

As the last portal discussed in detail herein, the possibility exists that a manufacturer portal is provided as a software unit or is connected via a programming interface. Via the manufacturer portal a manufacturer can conduct an evaluation of the data sets of the database that represent some or all of configuration data. The manufacturer thus receives an improved overview of the entire installed base, possibly also of the competition. It can be determined how many devices of a type are still active as a whole, how they are modified, for which purpose they are used most, which problems occur etc. Based on this, technical support can be improved, developments and research can be promoted where they are necessary, and the appeal of devices and how long they are in operation can be tracked. The most multifaceted possibilities for evaluation are conceivable here.

It is also possible for the manufacturer to send an offer to at least one specific operator based on the evaluation result via the manufacturer portal. In addition to the possibility to offer updates or replacements for older devices, geographic analyses can also be conducted, for example. For example, if it is established that no device of a specific type is present in specific areas, even though a demand exists (as can be concluded from data acquired via the end user portal, for example), corresponding offers can be sent to operators in this area. Many possibilities are also conceivable here.

It is again noted that in a manufacturer-spanning system, the operators of the system can regulate the manufacturer-specific access so that the data do not distort or unfairly shape the competition.

Already mentioned was the advantageous possibility to use an interface program fashioned for communication with the database, which interface program is installed or can be installed on a device. Such an interface program can be downloaded and installed via an operator portal, for example. Via this the device communicates directly and/or indirectly with the database. In direct communication, an additional role is provided, namely a device role that allows a device-specific access to the database, in particular mediated by a programming interface. An indirect communication can occur via the operator portal, for example; the operator role is then consequently used. The use of such an interface program offers a large number of advantageous embodiment possibilities, of which a few should be presented in the following.

The interface program can be fashioned for automatic (in particular cyclical) and/or operator-initiated determination of the configuration data of the device, and/or for automatic and/or operator-initiated communication (in particular after a security query posed to the operator) of the configuration data to the database. The transmission of the configuration data to the database can be largely automated in this manner. For example, the configuration data exist as a file in the device and are in particular updated cyclically by the interface program, for example once per day or weekly. The communication can likewise ensue automatically via the interface program but can also ensue when initiated by the operator. In each case, even given the automatic communication, it is advantageous to also obtain the confirmation of the operator for the communication, for example in the form of a dialog window presented on the device. Keeping the configuration data up to date is possible in this manner with minimal effort from the operator.

Furthermore, the interface program can also be fashioned for automatic configuration of the device based on a configuration data set stored in the database. Such an embodiment primarily concerns the software configuration of a device. It can often be necessary (for example within the scope of clinical studies in which examinations at various hospitals or medical facilities should be compared) to use devices with identical configurations. For example, a contact with another operator whose configuration can be adopted (possibly only temporarily) can now be established via the operator portal. An identifier of the associated data set of the other operator can be communicated to the interface program which retrieves the corresponding configuration data from the database and automatically configures the device based on this configuration data set. In practice a "cloning" of a configuration can thus ensue via the system according to the invention. It is noted that the communication of the necessary communication data to the interface program can naturally also ensue indirectly, for example via the operator portal.

In a further embodiment, the interface program is fashioned to store control data (in particular usage protocols) stored as additional device information and/or device data in the device, and/or to control the device using the control data, wherein the selection of the configuration data set and/or of the control data can in particular be implemented again via an operator portal. In this manner it is very comfortable to exchange control data and to store it on the concrete device for later retrieval, or even to directly control the device using thee control data. In the field of magnetic resonance examinations, for example, protocols or sequences that another operator provides in the database can be selected via the operator portal and then be retrieved directly from the database via the interface program, or be relayed via the operator portal to the interface program. In the simplest case, an examination protocol is selected via a double click in the operator portal (presented on a screen of the device, for example); this examination protocol arrives at the device in the described ways via the interface program; and said examination protocol can be directly used to control the device or can first be stored there. The exchange of information and in particular control data can be immensely simplified for the operators of the devices in this way via the system according to the invention.

However, it frequently occurs (as already discussed in the introduction) that the configurations (and thus the configuration data) of various devices, between which control data should be exchanged, differ at least in the details. This can have an effect on the applicability of the control data upon transfer from one device to another. It can therefore be advantageous for the interface program and/or an operator portal to be fashioned to adapt the control data to the configuration data of the device given a deviation between the configuration data of the device and the configuration data associated with the control data. In other words, at least small configuration differences can be automatically compensated for by the system (via the operator portal and/or the interface program) so that the desired control data are nevertheless also applicable to the other device. For example, acquisition times are correspondingly adapted to an x-ray device at different powers, or pulse sequences are adapted to an antenna geometry. A plurality of possibilities is conceivable.

An adaptation can also ensue based on regional rules (in particular local laws) at the location of the device. For example, regulations for radiation exposure of the patient can be provided; to comply with these the interval between individual pulses of a magnetic resonance frequency is increased or the like.

Very generally, the system according to the invention can also be used to transfer software updates for a device with mediation of the database and/or to install said software updates on the device. The specific configuration can thereby be respectively taken into account in order to use the correct software update for the specific system or to correspondingly adapt the software update so that complications do not arise.

BRIEF DESCRIPTION OF THE DRAWINGS

The single FIGURE shows a basic diagram of an embodiment of the system according to the invention.

DESCRIPTION OF THE PREFERRED EMBODIMENTS

The core of the exemplary embodiment of a system according to the invention that is shown in the FIGURE is a database 1 in which additional device information and/or device data that are associated with the configuration data are stored in addition to configuration data describing the hardware and software configuration of various medical technology devices. The location of the device, information regarding the institution operating the device, prince information regarding the use of the device, the type of use of the device, information regarding the salability of the device, control data (in particular examination protocols) and information about the operator can presently be indicated in the database 1 as additional device information and/or data that are to be voluntarily specified.

The system is directed toward three different groups of users that are designated in the following as operators, end users and manufacturers. Operators are the institutions or persons who operate the medical technology devices (magnetic resonance apparatuses in the present case), thus radiology practices, hospitals or research institutions, for example. The circle of the operators can naturally also be expanded beyond the immediate medical technology field since older medical devices that no longer satisfy the standard for patient use or are technically outdated are frequently used in tertiary application fields in which the operators can nevertheless be interested in the functions of the system according to the invention. The term "end user" essentially refers to patients or referrers. Referrers are those persons who can refer a patient to a specific medical technology device for the purpose of an examination, in particular thus physicians who are not themselves in possession of a suitable device but also health insurers who want to select the most advantageous provider themselves, for example. The third group is the manufacturers, wherein the system according to the invention (in particular the database 1) is designed to span across manufacturers; the data of the devices of various manufacturers are thus stored.

Different information from the database 1 is now of interest for each of the three cited user groups; however, only limited access rights are also present in order to avoid an abuse of the system. Therefore the system according to the invention offers a functionality that associates a role with each of the three user groups. An operator role, an end user role and a manufacturer role consequently exist. Each of these roles defines a role-specific access to the database, which means specific access rights and access prohibitions that correspond to the information possibilities accorded to this role. These roles are realized via role-based interfaces that in turn are part of a corresponding software means regulating the access of one of or the user groups to the database 1.

A differentiation is to be made with regard to these software means, as is to be learned from the FIGURE.

It is initially noted that in this exemplary embodiment of the present invention an Internet platform is in principle associated with each user group, namely an operator portal 2, an end user portal 3 and a manufacturer portal 4 via which access can respectively be had from the Internet 5. Three different Internet accesses to the database 1 thus exist that are associated with the respective user groups. However, the database operator does not presently operate all of these Internet platforms himself, rather only the operator portal 2 and the manufacturer portal 4. For the end user portal 3, the database operator merely provides a programming interface 6 as a software means via which an external end user portal 3 obtains access to the database 1, regulated by the end user role-based interface 7. The remaining role-based interfaces 7 are respectively realized in the Internet platforms themselves, thus the operator portal 2 and the manufacturer portal 4.

It is noted that the exemplary embodiment presented here is not limiting. An arbitrary number of roles can thus be provided, of which an arbitrary subset is accessible via programming interfaces through an external Internet platform and an arbitrary number are accessible to an Internet platform operated by the database operator itself. Moreover, it is also possible that a role can receive access to the database 1 via both an Internet platform operated on the part of the database operator and via an external Internet platform. Arbitrary embodiments are conceivable here. Furthermore, it is noted that the Internet platforms operated by the database operator (here the operator portals 2 and 4) do not need to be located on the same computer as the database 1. Internal programming interfaces can be provided, however, via which an access from the outside is not possible (and this differentiates them from the programming interface 6). It is noted that it is naturally also conceivable to fashion a programming interface as a single software means appropriate for all roles.

In particular with regard to the end user portal or portals (naturally multiple of these can also be present) primarily used by the patients and referrers it is noted that an outsourcing can be particularly advantageous since an integration into other systems (for example for the administration of electronic patient files or to retrieve medical advice) can ensue. Such additional systems are heavily frequented and therefore are oriented toward a larger end user group that receives an additional advantageous functionality via access to the database 1. This moreover also motivates operators who use the system 1 since here they can be made known as vendors to a wider group.

As mentioned, the database 1 is based on the presence of optimally up-to-date configuration data of as many medical technology devices as possible, in particular nuclear magnetic resonance apparatuses. The advantages resulting for the cited user groups from such a database 1 with continuously updated configuration data are explained in detail in the following using the operator portal 2, the end user portal 3 and the manufacturer portal 4.

An operator who would like to use the system according to the invention must initially register by name via the operator portal 2. In this way the configuration data can be associated with him, which is of great importance for a large number of applications of the system according to the invention. The operator portal 2 then offers him the possibility to upload configuration data and the possible cited additional device information and/or device data into the database 1 in his role as operator. The possibility is additionally provided to him to view and to download at least portions of the data sets of other operators that have been provided by said other operators, for example for the purpose of an exchange.

The operator portal 2 offers multiple possibilities for the uploading of configuration data. At this point it is already noted that an automatic updating using an interface program 9 can also ensue given medical technology devices 8 involved in a communication connection with the Internet 5, which is explained below in further detail with regard to the functionalities of the interface program 9. If the operator does not wish to use the interface program 9 in any case, or if the operator's medical technology device 8 is not connected to the Internet 5, the possibilities of the operator portal 2 are still open to the operator.

The option is initially provided to generate a configuration file by means of an or the interface program 9. The operator can thereby download the interface program via the operator portal and install it on his device (insofar as the interface program is not already installed on his device). The interface program comprises an option with which a configuration file can be generated, in particular thus a type of "fingerprint" of the system that is ideally adapted (in terms of its structuring and the configuration data stored therein) to placement in the database 1. This configuration file is then uploaded via the operator portal 2 and can be imported directly into the database 1.

In another variant, a copy of a screen content of the device can be generated on the part of the operator. These devices include the possibility to display a configuration and/or status screen. Its contents are all or at least a large part of the required configuration data. This screen can now be stored as a graphic file, for example via a function present in many operating systems. Alternatively, it is naturally also possible to generate a hard copy of the screen content in order to then scan this in and upload it via the operator portal 2. If the screen content is first uploaded in the form of the graphic file, an image analysis (in particular a text recognition from which the configuration data are determined and can be imported into the database 1) which can consist of many individual program means can be implemented in the operator portal 2 itself. Such an image analysis functionality can naturally also be realized in the system via a separate program means, thus outside of the operator portal 2.

In a third variant, an operator can upload system data of the device via the operator portal 2. Such system data are present in log files or portions of the system registration, for example. In nuclear magnetic resonance apparatuses, measurement data or, respectively, reconstructed image data are also frequently stored in formats in which the file contains a header that indicates the system configuration upon acquisition of the data. On example of this is the DICOM format. The operator can likewise upload such files comprising system data of the device to the operator portal 2, where the system determines the corresponding configuration data from the file (analogous to the case of the screen content) and imports them into the database 1.

If the operator has uploaded the configuration data, or also at a later point in time, he can additionally conduct an analysis of the device configuration via the operator portal 2. The typical support is presently supplemented with released information of other operators, for example tips, ideal settings or even user protocols, in particular examination and measurement protocols or sequences. The operator thus receives information, tips and/or instructions for necessary or reasonable software updates, and possibly also recommendations regarding use of his device, in particular via examination or measurement protocols. Other operators can possibly also provide their configurations or the like. Moreover, the operator portal 2 also offers the possibility to directly adopt control data of other operators from the database into their own device, which can ensue either directly via communication of the interface program 9 with the database 1 or also indirectly via the operator portal 2. As is explained in further detail later, the interface program 9 can also directly control a device 8 according to the control data. A configuration of another operator can be analogously adopted.

After the uploading and storage of the configuration data in the database 1, an incentive is likewise associated with an operator as a reward for uploading. This may be money or also a virtual currency (for example bonus points), but possibly also software options or tools that can further facilitate the operation with the device or the support for the operator. The operator is thereby additionally motivated to always keep his or her configuration data up to date. In the system according to the invention the amount or, respectively, the value of the incentive is thereby determined using the quality of the configuration data, wherein in particular the completeness and the clarity of the ability to be associated with a device class (for example the determination of the model) can be taken into account. The operator is thus additionally motivated to deliver his configuration data as completely as possible.

Via the operator portal 2 it is also possible to organize purchases and sales of devices. Devices for sale can thereby be specifically sought; however, depending on the analysis result of an analysis of the configuration data, better devices that are offered for sale by another operator can be recommended. A number of possibilities for this are conceivable here. For example, an auction platform can be integrated via which devices can be sold in the style of an auction.

The present external end user portal 3 is provided as an additional portal. The database 1 can primarily be accessed via the end user portal 3 in order to be able to locate a suitable medical technology device for an examination. For example, a query can thereby be posed as to where in the region of the end user a 3 Tesla magnetic resonance apparatus that is configured to conduct chest examinations is to be found. Usage prices or the like can be retrieved. For example, the end user portal 3 can also be used by research facilities that require a specific of a device for special research and would like to locate such a device. Here as well a plurality of possibilities and search criteria are thus conceivable. In particular it is presently provided that the search queries are likewise recorded (in particular are anonymized) and stored in the database 1. This can be advantageously used in an evaluation of the data for the manufacturer in the manufacturer portal 4 in order to establish which configurations and functionalities are particularly requested (for example in the goals of a market analysis) in order to be able to appropriately direct marketing and research and development strategies, or even to be able to make offers to operators in regions in which a specific device or a specific configuration is absent, with the note that this configuration is sought in their region but is not yet present.

The evaluation of at least a portion of the data sets can ensue via the manufacturer portal 4 as already mentioned. The manufacturer thereby receives not only information about the installed base and the path of the devices, replacement parts and auxiliary devices that it has sold (in particular since the sales via the operator portal 2 can also be regulated so that it receives an overview of the used apparatuses and the used configurations); rather, it can also conduct continuing evaluations of the most varied type, for example with regard to support strategies, research and development goals and marketing strategies. In particular, it is possible to send an offer to an operator or also to multiple operators based on the evaluation result. A check can be made (for example when software updates should be sent to an operator) as to whether the software update is appropriate at all for the configuration of the operator. Here as well a number of possibilities exist for advantageous usage of the data to which the manufacturers have access via the corresponding manufacturer-based interface 7.

it is additionally noted that software updates for a device can also be automatically transferable and installable on the device under supervision of the database 1, in particular using an interface program 9.

This interface program 9 and its possibilities are now discussed in detail. As mentioned, the interface program 9 can be downloaded via the operator portal 2 and installed on a device 8, but it is equally possible for the device 8 to be already delivered with an installed interface program 9. A direct communication with the database 1 can be established via the interface program 9 (again via the Internet 5), for which in particular a programming interface (not shown in detail here) can be provided that allows a role-specific access for a device role. In addition to the user groups, an additional role is thus provided with a clearly defined access to the database 1, namely the role of the device.

However, an indirect communication with the database via the operator portal 2 is also conceivable in principle.

The interface program 9 can advantageously be used for different purposes within the scope of the system. It automatically, cyclically determines the configuration data of the device and transmits them (automatically or initiated by the operator, which in particular can be selected by the operator himself) to the database 1. A security query can be provided to the operator, for example a corresponding dialog window on the device 8 with which the sending of the configuration data to the database 1 is confirmed again.

An additional functionality of the interface program 9 is the automatic configuration of the device 8 based on a configuration data set stored in the database. The configuration of another operator thus can be cloned. This can be beneficial if the close offers a better configuration for the purposes that the operator of the device 8 is also pursuing, such as, for example, when clinical studies are conducted in which the results of the devices of two different operators should be compared.

Furthermore, the interface program 9 can also be used in order to transfer control data for the device 8 that are provided by another operator via the operator portal 2 (for example examination protocols or sequences for a nuclear magnetic resonance apparatus) to the device 8, and therefore to control said device 8 with these. The operator of the device 8 selects corresponding data via the operator portal 2, which data are then transmitted either directly via the interface program 9 or via the operator portal 2 to the device 8 and are stored there. As stated, a control of the device 8 can also directly ensue such that a suitable examination protocol is located in the operator portal 2 and can be clicked on (for example if an examination is pending) whereupon the examination via the device 8 automatically ensues with the selected examination protocol. In this way the exchange of such control data is simplified and the system can ultimately serve for direct control of the technical device 8.

It often occurs that the configuration data of a device from which the control data should be adopted and the device 8 differ, if only in details. The applicability of the control data to the device 8 is then no longer assured. Here as well the interface program 9 can possess a corresponding functionality in that an adaptation of the control data to the configuration data of the device 8 ensues insofar as this is possible. If it is not possible, an error message can ensue with an indication of the deviating configuration data. It is noted that such an adaptation functionality can also already be realized in the operator portal 2, in particular when the control data arrive at the device 8 indirectly via the operator portal 2.

The described adaptation can additionally take into account in which region the device 8 is located and whether there are possibly deviating regional regulations (in particular laws) that require a modification of the control data, for example with regard to the radiation exposure (SAR).

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for detection, administration and/or evaluation of a current configuration of a medical examination or therapy device, comprising the steps of:
    via an output port, selected from the group consisting of a programming interface and an internet platform, of a medical examination or therapy device comprised of a current combination of a plurality of device units, selected from the group consisting of hardware units and software units, said medical examination or therapy device being available in different versions respectively from different manufacturers and being modifiable to be comprised of different combinations of said plurality of device units at different times, transmitting configuration data to a database via a network placing said output port and said database in communication with each other, said configuration data identifying which of said hardware units and which of said software units are in said current combination;
    storing said configuration data for said medical examination or therapy device in said database with an association of the manufacturer, among said plurality of manufacturers, of said medical examination or therapy device; and
    through a database interface, allowing access to said configuration data stored in said database by different searchers searching for a specific medical examination or therapy device having a specific combination of said device units, and configuring said access differently for respectively different searchers defined by respectively different roles, and defining said roles as being in the group consisting of an operator role, an end user role consisting of referrers and patients, and a manufacturer role, to obtain a search result indicating whether said current combination identified by said configuration data in said database corresponds to said specific combination; and
    making said search result available from said database via an output of the database in a humanly perceptible form.

2. A system as claimed in claim 1 comprising storing said configuration data in said database linked to additional information or data for said medical examination or therapy device, selected from the group consisting of a location of said medical examination or therapy device, a designation of an entity responsible for operating said medical examination or therapy device, price information for using said medical examination or therapy device, a type of usage of said medical examination or therapy device, sales information, control data, usage protocols for controlling operation of said medical examination or therapy device, and information describing an operator of said device.

3. A system as claimed in claim 2 comprising an operator portal in communication with said input port allowing uploading or downloading of said configuration data and said additional information.

4. A system as claimed in claim 3 wherein said device comprises a processor connected to a display, said processor being configured by an interface program installed therein to cause a configuration file, or a screen shot of said configuration file, to be displayed in a form allowing determination of said configuration data by automatic image analysis, said configuration file comprising a header and log files and said interface program configuring said processor to determine said configuration data from one of said header or said log files.

5. A system as claimed in claim 3 wherein said operator portal is configured to allow tracking, via said database, of purchases and sales of said medical examination or therapy device.

6. A system as claimed in claim 3 wherein said device comprises a processor configured to generate recommendations and associated information dependent on said configuration data, and wherein said operator portal is configured to make said recommendations and said additional data available in humanly perceptible form.

7. A system as claimed in claim 6 wherein said operator portal is configured to present an award to an operator for uploading said configuration data via said operator portal, said reward being selected from the group consisting of a monetary amount, a software option, and a tool.

8. A system as claimed in claim 7 wherein said processor determines a level of said reward dependent on a quality of said configuration data selected from the group consisting of completeness of said configuration data and clarity if said configuration data.

9. A system as claimed in claim 1 comprising an end user portal configured to allow an end user to search for devices represented by said configuration data according to predetermined search criteria.

10. A system as claimed in claim 1 comprising a manufacturer portal configured to allow a manufacturer to conduct an evaluation of subsets of said configuration data.

11. A system as claimed in claim 10 wherein said manufacturer portal is configured to allow a manufacturer to transmit an offer to predetermined operators of medical examination or therapy devices represented by said configuration data.

12. A system as claimed in claim 1 wherein said device comprises a processor configured by an interface program installed therein allowing direct communication between said processor of said medical examination or therapy device and said database, via said operator portal.

13. A system as claimed in claim 12 wherein said processor is configured by said interface program for automated cyclical determination of said configuration data or operator-initiated communication of said configuration data to said data base.

14. A system as claimed in claim 12 wherein said processor is configured by said interface program for automatic configuration of said medical examination or therapy device using a configuration dataset from among said configuration data stored in said database, or to retrieve control data from said database and to store the retrieved control data in the medical examination or therapy device, or to control the medical examination or therapy device using control data in said configuration data, via said operator portal.

15. A system as claimed in claim 14 wherein said processor is configured by said interface program to adapt said control data to said configuration data for said medical examination or therapy device.

16. A system as claimed in claim 15 wherein said processor is configured to adapt said control data dependent on geographically local rules in effect at the location of the medical examination or therapy device.

17. A system as claimed in claim 1 wherein said device is configured to receive software updates dependent on the configuration data stored in the database.

* * * * *